US006509191B2

(12) United States Patent
Liu et al.

(10) Patent No.: US 6,509,191 B2
(45) Date of Patent: Jan. 21, 2003

(54) IDENTIFICATION AND CHARACTERIZATION OF A PAGODA PHENOTYPE (PGD) IN PLANTS

(76) Inventors: Alex Liu, 2061 W. 16th Ave., Eugene, OR (US) 97402; Helena Mathews, 14546 NW. Joseph Ct., Portland, OR (US) 97229; Jill Van Winkle, 2185 NW. Flanders, #3, Portland, OR (US) 97210; Ry Wagner, 1972 Alder St., Eugene, OR (US) 97405; Stanley R. Bates, 2124 45th Ave. SE., Salem, OR (US) 97301; Susan Bovee-Picciano, 835 14th St., Lafayette, OR (US) 97127

( * ) Notice: Subject to any disclaimer, the term of this patent is extended or adjusted under 35 U.S.C. 154(b) by 0 days.

(21) Appl. No.: 09/847,057

(22) Filed: May 1, 2001

(65) Prior Publication Data

US 2002/0004943 A1 Jan. 10, 2002

Related U.S. Application Data

(60) Provisional application No. 60/201,329, filed on May 2, 2000.

(51) Int. Cl.$^7$ ............................ C12N 5/04; C12N 15/82; C12N 15/00; C07H 21/04
(52) U.S. Cl. ..................... 435/419; 435/320.1; 435/468; 536/23.6; 536/24.1
(58) Field of Search ..................... 536/23.6; 435/320.1, 435/419, 468; 800/290, 298

(56) References Cited

U.S. PATENT DOCUMENTS 5,618,716 A * 4/1997 Burlingame ................ 435/106
5,856,148 A * 1/1999 Burlingame ................ 435/106

OTHER PUBLICATIONS

Broun et al, "Catalytic Plasticity of Fatty Acid Modification Enzymes Underlying Chemical Diversity of Plant Lipids", Nov. 1998, Science vol. 282, pp. 1315.*
Lazar et al, "Transforming Growth Factor x: Mutation of Aspartic Acid 47 and Leucine 48 Results in Different Biological Activities", Mar. 1988, Molecular and Cellular Biology, vol. 8 No. 3 pp. 1247–1252.*
Bowie et al, "Deciphering the Message in Protein Sequences: Tolerance to Amino Substitutions", Mar. 1990, Science vol. 247, pp. 1306–1310.*
Vollbrecht et al, "The development gene Knotted–1 is a member of a maize homeobox gene family", Mar. 1991, Nature vol. 350, pp. 241–243.*
Finnegan et al, Transgene Inactivation:Plants Fight Back, Sep. 1994, Bio/Technology vol. 12, pp. 883–888.
Hill et al, Functional Analysis of Conserved Histidines in ADP–Glucose Pyrophosphorylase from *Escherichia Coli*, 1988, Biochemical and Biophysical Research Communications vol. 244, pp. 573–577.
Burgess et al, Possibile Dissociation of the Heparin–binding and Mitogenic . . . by Site–directed Mutagenesis of a Single Lysine Residude, 1990, The Journal of Cell Biology, vol. 111, pp. 2129–2138.
Weigel et al, "Activation Tagging in Arabidopsis", Apr. 2000, Plant Physiology, vol. 122, pp. 1003–1013.
Eshed et al, "Establishment of polarity in lateral organs of plants", 2001, Current Biology vol. 11 No. 16 pp. 1251–1260.*
Janssen et al, "Overexpression of a Homebox Gene, LeT6, Reveals Indeterminate Features in the Tomato Compound Leaf", 1998, Plant Physiol. vol. 117, pp. 771–786.*
Nguyen et al, "Genetic Analysis of 12 Polymorphic Isozyme Loci in Taro, *colocasia esculenta* (L.) Schott", 1999, Breeding Science vol. 49, pp. 179–185.*
Raven et al, Biology of Plants 1999 p. 543.*
Begun et al "Evolutionary Inferences from DNA Variation at the 6–Phosphogluconate . . . Selection and Geographic Differention", Jan. 1994, Genetic vol. 136, vol. 155–171.*
Boskovic et al, "Inheritance of isoenzymes and their linkage relationships in two interspecific chery progenies" 1997, Euphyrica vol. 93, pp. 129–143.*
Database EMBL Sequence Library 'Online! Feb. 3, 1998 Kaneko T., et al.: "Structural Analysis of *Arabidopsis thaliana* chromosome 5. V. Sequence features of the regions of 1,381,565 bp covered by twenty one physically assigned P1 and TAC clones" XP002188218, accession No. AB010700.
Database Trembl Database 'Online! Mar. 1, 2000 Kaneko, T., et al.: "Structural analysis of *Arabidopsis thaliana* chromosome 5. V. Sequence features of the regions of 1,381,565 bp covered by twenty one physically assigned P1 and TAC clones—Genomica DNA, Chromosoem 5, P1 CLONE: MUD21" XP002188379, accession No. Q9FKZ3.

* cited by examiner

*Primary Examiner*—Elizabeth F. McElwain
*Assistant Examiner*—Stuart Baum
(74) *Attorney, Agent, or Firm*—Exelixis, Inc.; Jan P. Brunelle; Sarah Elson

(57) ABSTRACT

The present invention is directed to a novel plant phenotype, designated PAGODA (PGD), a nucleic acid sequence expressed in plants demonstrating the PGD phenotype and the corresponding amino acid sequence. Also provided are plant cells and plants that exhibit modified PGD expression.

4 Claims, No Drawings

SEQUENCE LISTING

<160> NUMBER OF SEQ ID NOS: 4

<210> SEQ ID NO 1
<211> LENGTH: 1083
<212> TYPE: DNA
<213> ORGANISM: Arabidopsis thaliana

<400> SEQUENCE: 1

```
atggcgtctt caagctctcc ttgcgcagct tgtaaattct tgagaagaaa atgcacacaa      60
gaatgtgtat tcgctccata tttcccacca gaccaacctc aaaaattcgc attcgttcac     120
aaagtctttg gagcaagtaa cgtcgctaag cttctcaacg agcttgcctc taaccaaaga     180
gaagacgcag tgaactctct tttctacgaa gctgaagcta ggttacgtga tccggtttac     240
ggttgcgtcg gtttaatctc aatccttcaa catcgtctta acaagttaa  ccacgatctt     300
gaaaacgcta agaaagagct cgctacgtac gttggtcctc aagctatgct cccaattctt     360
caaccgcatt tcatgtctct accacctcaa ccgcaacgac cgtcttcttc ttcagcgtct     420
gtgttgactc agcatcatca taacttgttg ccgatgatgg ctattccaac aggacaactg     480
taccatcaac aacaacaaca gatctttgag gctcagcagt tagcagcggt tgcgagagag     540
caacagaatg agatgtttag agcttatgga ggaggaggag gaagtagtag tccacaccat     600
caaaaccaag ctcaagctga gattttgagg tttaataatg gttttgactc tgtaccggcc     660
ggttcagtta cggttactgg gtttaatcag ttaagttctg gtggtacagc ggtaaccgga     720
atgtctcttg gagtccttcg acgaataata attaccatac ggatcagcaa ttacaccatc     780
atcatcaacc gcaacaacat catgaggctc aactattcat accttcacaa tcttctcagc     840
cgctaccgct ccaaacgcag gagacgcaaa cgcagacgca gccgaattcg gagagcgagg     900
aggttggaaa ctctgacttt gctcaaggca ttatggacgc aatcgagttt ttctttcttc     960
ctgattttgt cggacgtcca acagcgaaaa gacactcacc acgtaaaagt caaacgacta    1020
acaaagaagt cagcttattt ggttgatttt gagtcctgca gacagttttg gtataaagta    1080
taa                                                                  1083
```

<210> SEQ ID NO 2
<211> LENGTH: 360
<212> TYPE: PRT
<213> ORGANISM: Arabidopsis thaliana

<400> SEQUENCE: 2

```
Met Ala Ser Ser Ser Pro Cys Ala Ala Cys Lys Phe Leu Arg Arg
1               5                  10                  15

Lys Cys Thr Gln Glu Cys Val Phe Ala Pro Tyr Phe Pro Pro Asp Gln
                20                  25                  30

Pro Gln Lys Phe Ala Phe Val His Lys Val Phe Gly Ala Ser Asn Val
            35                  40                  45

Ala Lys Leu Leu Asn Glu Leu Ala Ser Asn Gln Arg Glu Asp Ala Val
        50                  55                  60

Asn Ser Leu Phe Tyr Glu Ala Glu Ala Arg Leu Arg Asp Pro Val Tyr
65                  70                  75                  80

Gly Cys Val Gly Leu Ile Ser Ile Leu Gln His Arg Leu Lys Gln Val
                85                  90                  95

Asn His Asp Leu Glu Asn Ala Lys Lys Glu Leu Ala Thr Tyr Val Gly
            100                 105                 110
```

```
Pro Gln Ala Met Leu Pro Ile Leu Gln Pro His Phe Met Ser Leu Pro
        115                 120                 125
Pro Gln Pro Gln Arg Pro Ser Ser Ser Ala Ser Val Leu Thr Gln
    130                 135                 140
His His His Asn Leu Leu Pro Met Met Ala Ile Pro Thr Gly Gln Leu
145                 150                 155                 160
Tyr His Gln Gln Gln Gln Ile Phe Glu Ala Gln Gln Leu Ala Ala
                165                 170                 175
Val Ala Arg Glu Gln Gln Asn Glu Met Phe Arg Ala Tyr Gly Gly Gly
            180                 185                 190
Gly Gly Ser Ser Pro His His Gln Asn Gln Ala Gln Ala Glu Ile
        195                 200                 205
Leu Arg Phe Asn Asn Gly Phe Asp Ser Val Pro Ala Gly Ser Val Thr
    210                 215                 220
Val Thr Gly Phe Asn Gln Leu Ser Ser Gly Gly Thr Ala Val Thr Gly
225                 230                 235                 240
Met Ser Leu Gly Val Leu Arg Arg Ile Ile Ile Thr Ile Arg Ile Ser
                245                 250                 255
Asn Tyr Thr Ile Ile Ile Asn Arg Asn Asn Ile Met Arg Leu Asn Tyr
            260                 265                 270
Ser Tyr Leu His Asn Leu Leu Ser Arg Tyr Arg Ser Lys Arg Arg
        275                 280                 285
Arg Lys Arg Arg Arg Ser Arg Ile Arg Arg Ala Arg Leu Glu Thr
    290                 295                 300
Leu Thr Leu Leu Lys Ala Leu Trp Thr Gln Ser Ser Phe Ser Phe
305                 310                 315                 320
Leu Ile Leu Ser Asp Val Gln Gln Arg Lys Asp Thr His Val Lys
                325                 330                 335
Val Lys Arg Leu Thr Lys Lys Ser Ala Tyr Leu Val Asp Phe Glu Ser
            340                 345                 350
Cys Arg Gln Phe Trp Tyr Lys Val
        355                 360

<210> SEQ ID NO 3
<211> LENGTH: 3920
<212> TYPE: DNA
<213> ORGANISM: Arabidopsis thaliana

<400> SEQUENCE: 3
ctcgagacga agacagcagt tagagaggct aattaagtca aatttaaaaa tgaaaataat      60
ttcagggata aatctgtcat tacatgtacg gttgcttaaa acttaaaacc caaattaata    120
attatgagat ccaacggcgg caaatcaccc tctcttgtaa tctcgacggc tatggtttgt    180
agcgtattca ctaatataaa agatcgtctc cgtcattaga aaagccttcc ttttttttc     240
ccatttcctt cttcttgatg atcttttatt gattctctct tcgttttaaa aaaatcttca    300
gccttagggc agaataaatc ggagatcaga tccataatc gggttttct gggttttctc     360
agaaacccta gacccgatag taacttccta ctcactcaac ctatctctct attgatcatg    420
gaatcaaacg atgaagagag tgagacacga agctagcaac aaaaatatca taaagagggt    480
tttggaaagg agaaagattc gttttaatt gaggtaagtt tgattttcc ttttcttgat      540
cgatgatttg atttagttaa aaagtttgat tgatattgat agattttact ttgatcgttt    600
atgataattt ttagtatctt gttttaattt ctggaatctg ttgatcttct tcttcttata    660
ccttgccttg taaacagatc tgaaaacttc tattggctat cttgatcttg gtttataatc    720
```

```
agaaaattga tttcttttc cttctatttc actattctat tacttgtacg gaaattttcg    780
ttgcacgaat cacgataaca tttatttaca atctcttcaa cttcataggg tctctcatct    840
aatgacttac acgaagcttc ctcgatgcat ttattttcac gatccctatt tcattatttt    900
caagaaaatt tattaaaaga gactgaatct ttttatttct ttataatctt ttcaggctct    960
caagtctgaa aagagacaaa aaaatggcg tcttcaagct ctccttgcgc agcttgtaaa   1020
ttcttgagaa gaaatgcac acaagaatgt gtattcgctc catatttccc accagaccaa   1080
cctcaaaaat tcgcattcgt tcacaaagtc tttggagcaa gtaacgtcgc taagcttctc   1140
aacgagcttg cctctaacca aagagaagac gcagtgaact ctcttttcta cgaagctgaa   1200
gctaggttac gtgatccggt ttacggttgc gtcggtttaa tctcaatcct tcaacatcgt   1260
cttaaacaag ttaaccacga tcttgaaaac gctaagaaag agctcgctac gtacgttggt   1320
cctcaagcta tgctcccaat tcttcaaccg catttcatgt ctctaccacc tcaaccgcaa   1380
cgaccgtctt cttcttcagc gtctgtgttg actcagcatc atcataactt gttgccgatg   1440
atggctattc caacaggaca actgtaccat caacaacaac aacagatctt tgaggctcag   1500
cagttagcag cggttgcgag agagcaacag aatgagatgt ttagagctta tggaggagga   1560
ggaggaagta gtagtccaca ccatcaaaac caagctcaag ctgagatttt gaggtttaat   1620
aatggttttg actctgtacc ggccggttca gttacggtta ctgggtttaa tcagttaagt   1680
tctggtggta cagcggtaac cggaatgtct cttggaggta actttgttga tagtccttcg   1740
acgaataata attaccatac ggatcagcaa ttacaccatc atcatcaacc gcaacaacat   1800
catgaggctc aactattcat accttcacaa tcttctcagc cgctaccgct ccaaacgcag   1860
gagacgcaaa cgcagacgca gccgaattcg gagagcgagg agggtagaag gaatgtcatt   1920
ggttaatctc gctaattgag gaataataaa aaagagggat actaaaaaca aagatacggc   1980
ctttgacctt ctcgcttgct cgataaactc tcaaaacaat ccctaaggta cgtggcaaaa   2040
aactcgattt taagtttcaa ccggataaat aattagggtt tcgatatttg tttcatatag   2100 tttttctt tcattttctc tgcattttga atgttcttta tttatggtat agtacagtta   2160
cagtggtaca gaggaggttt tgctctttat atataacatt taatgaaaaa gccttgtcat   2220
ttcttcaata actctcctgc tcttatagcc atagcccata tttttaaact acttcctttt   2280
tgttggattc tctgaacaat aatgcattaa ctaacctagt tattattaat aatttagggt   2340
ttaaaagaaa ataaatcgtg gtgggtcaca tcacttcacc aattcttgat atggtaatta   2400
tttgatatat gttggctttg ttctacctac tagagatgaa aaagagaatt tgtgtgtatc   2460
agagtctaag atttgcttac acctttctgt ctggaaatct tttaagtgtt gtcccagaag   2520
atgcacttta tacttgcatg tattatcaat ttagcatcaa tcgcatcgat caagttcttt   2580
atattaataa tattgtttct taagtctctc ttttggtttt acttatattt cctcgacttt   2640
tcttgcagtt ggaaactctg actttgctca aggcattatg gacgcaatcg agttttctt   2700 tcttcctgat tttgtcggac gtccaacagc gaaaagacac tcaccacgta aagtcaaac   2760 gactaacaaa gaagtcagct tatttggttg attttgagtc ctgcagacag ttttggtata   2820
aagtataaac caaaggcctc gtatcaattt gaacaaaaga tctccactcc atcccgaaac   2880
aaatactacc ttgcttttt ttttcttgt accctattaa tattttttg acatttcttt   2940 tggttcaagt aaaaaaaagg agaaattagt gttttggtt gcaaatctat ttgtaaatta   3000
gatgtcaaga gaagtgttac ttgccctagt ggtttatcac atatccgacg tcaaccgaa   3060
```

-continued

| | |
|---|---|
| atattaaatt aaaaagtatg aataatctat ctttgtatat ccgcatttac attttttttt | 3120 |
| gtttctggaa aagtatcgat cctgttatat ataccctaaag tttaaaatgc gaaataagaa | 3180 |
| acaaaaagag tttagtttat gaaaacatta tcataatgat accaaaaagg ctaaggaaaa | 3240 |
| acaaattaca aaaaggctac atcattttt aaaagagagt gtgtgcttca catataaaca | 3300 |
| aggaaacgca tataataatc atcaagtagc tagatgaagc taaagaagta gttaagtgtg | 3360 |
| aatgcttggc aattaagatt gtgttggttc atttattaac aatctttgac cactcactaa | 3420 |
| tttatttttg gctctctctt ctatatcatc accgttttat ctttataaac catccctcaa | 3480 |
| gactctccca atattacatg atgtgtttaa tcctcacgaa ttcgcatgaa tcaaaaccgg | 3540 |
| ctgaaaaaca gatgtaacat ttaagttaac atactcacac caatctaaat tattagactt | 3600 |
| tcattcactt taacacattt gtccatacca tgatgatcat aacaatcagt agctaaatca | 3660 |
| atgtgagtgt ggcttagata tttgatctga atgattcatg agaaacatgg atacttaatg | 3720 |
| ttcatgtgca tgtgcatata atagtatatt aatctcacca gtaggatgct tagtatagca | 3780 |
| ataaagagaa ggtggtgaaa ttgatgagca tcggccatta aattaagcac tgacccatta | 3840 |
| attgcgcact tacccataaa caccattcac tccttttcat taacttaaga gtaaaattat | 3900 |
| acatacacct cgctatctct | 3920 |

<210> SEQ ID NO 4
<211> LENGTH: 8340
<212> TYPE: DNA
<213> ORGANISM: Binary vector pAGI4002

<400> SEQUENCE: 4

| | |
|---|---|
| agtactttga tccaacccct ccgctgctat agtgcagtcg gcttctgacg ttcagtgcag | 60 |
| ccgtcttctg aaaacgacat gtcgcacaag tcctaagtta cgcgacaggc tgccgccctg | 120 |
| ccctttcct ggcgttttct tgtcgcgtgt tttagtcgca taaagtagaa tacttgcgac | 180 |
| tagaaccgga gacattacgc catgaacaag agcgccgccg ctggcctgct gggctatgcc | 240 |
| cgcgtcagca ccgacgacca ggacttgacc aaccaacggg ccgaactgca cgcggccggc | 300 |
| tgcaccaagc tgttttccga agatcaccc ggcaccaggc gcgaccgccc ggagctggcc | 360 |
| aggatgcttg accacctacg ccctggcgac gttgtgacag tgaccaggct agaccgcctg | 420 |
| gcccgcagca cccgcgacct actggacatt gccgagcgca tccaggaggc cggcgcgggc | 480 |
| ctgcgtagcc tggcagagcc gtgggccgac accaccacgc cggccggccg catggtgttg | 540 |
| accgtgttcg ccggcattgc cgagttcgag cgttccctaa tcatcgaccg cacccggagc | 600 |
| gggcgcgagg ccgccaaggc ccgaggcgtg aagtttggcc cccgccctac cctcacccog | 660 |
| gcacagatcg cgcacgcccg cgagctgatc gaccaggaag ccgcaccgt gaaagaggcg | 720 |
| gctgcactgc ttggcgtgca tcgctcgacc ctgtaccgcg cacttgagcg cagcgaggaa | 780 |
| gtgacgccca ccgaggccag gcggcgcggt gccttccgtg aggacgcatt gaccgaggcc | 840 |
| gacgccctgg cggccgccga gaatgaacgc caagaggaac aagcatgaaa ccgcaccagg | 900 |
| acggccagga cgaaccgttt tcattaccg aagagatcga ggcggagatg atcgcggccg | 960 |
| ggtacgtgtt cgagccgccc gcgcacgtct caaccgtgcg gctgcatgaa atcctggccg | 1020 |
| gtttgtctga tgccaagctg gcggcctggc cggccagctt ggccgctgaa gaaaccgagc | 1080 |
| gccgccgtct aaaaaggtga tgtgtatttg agtaaaacag cttgcgtcat gcggtcgctg | 1140 |
| cgtatatgat gcgatgagta aataaacaaa tacgcaaggg gaacgcatga aggttatcgc | 1200 |
| tgtacttaac cagaaaggcg ggtcaggcaa gacgaccatc gcaacccatc tagcccgcgc | 1260 |

-continued

```
cctgcaactc gccggggccg atgttctgtt agtcgattcc gatccccagg gcagtgcccg    1320
cgattgggcg gccgtgcggg aagatcaacc gctaaccgtt gtcggcatcg accgcccgac    1380
gattgaccgc gacgtgaagg ccatcggccg gcgcgacttc gtagtgatcg acggagcgcc    1440
ccaggcggcg gacttggctg tgtccgcgat caaggcagcc gacttcgtgc tgattccggt    1500
gcagccaagc ccttacgaca tatgggccac cgccgacctg gtggagctgg ttaagcagcg    1560
cattgaggtc acgatggaa ggctacaagc ggccttgtc gtgtcgcggg cgatcaaagg     1620
cacgcgcatc ggcggtgagg ttgccgaggc gctggccggg tacgagctgc ccattcttga    1680
gtcccgtatc acgcagcgcg tgagctaccc aggcactgcc gccgccggca caaccgttct    1740
tgaatcagaa cccgagggcg acgctgcccg cgaggtccag gcgctggccg ctgaaattaa    1800
atcaaaactc atttgagtta atgaggtaaa gagaaaatga gcaaaagcac aaacacgcta    1860
agtgccggcc gtccgagcgc acgcagcagc aaggctgcaa cgttggccag cctggcagac    1920
acgccagcca tgaagcgggt caactttcag ttgccggcgg aggatcacac caagctgaag    1980
atgtacgcgg tacgccaagg caagaccatt accgagctgc tatctgaata catcgcgcag    2040
ctaccagagt aaatgagcaa atgaataaat gagtagatga atttagcgg ctaaaggagg     2100 cggcatggaa aatcaagaac aaccaggcac cgacgccgtg aatgccca tgtgtggagg     2160 aacgggcggt tggccaggcg taagcggctg ggttgtctgc cggcctgca atggcactgg    2220 aaccccccaag cccgaggaat cggcgtgacg gtcgcaaacc atccggcccg gtacaaatcg    2280
gcgcggcgct gggtgatgac ctggtggaga agttgaaggc cgcgcaggcc gcccagcggc    2340
aacgcatcga ggcagaagca cgccccggtg aatcgtggca agcggccgct gatcgaatcc    2400
gcaaagaatc ccggcaaccg ccggcagccg gtgcgccgtc gattaggaag ccgcccaagg    2460
gcgacgagca accagatttt ttcgttccga tgctctatga cgtgggcacc cgcgatagtc    2520
gcagcatcat ggacgtggcc gttttccgtc tgtcgaagcg tgaccgacga gctggcgagg    2580
tgatccgcta cgagcttcca gacgggcacg tagaggtttc gcagggccg gccggcatgg    2640 ccagtgtgtg ggattacgac ctggtactga tggcggtttc ccatctaacc gaatccatga    2700
accgataccg ggaagggaag ggagacaagc ccggccgcgt gttccgtcca cacgttgcgg    2760
acgtactcaa gttctgccgg cgagccgatg gcggaaagca gaaagacgac ctggtagaaa    2820
cctgcattcg gttaaacacc acgcacgttg ccatgcagcg tacgaagaag gccaagaacg    2880
gccgcctggt gacggtatcc gagggtgaag ccttgattag ccgctacaag atcgtaaaga    2940
gcgaaaccgg gcggccggag tacatcgaga tcgagctagc tgattggatg taccgcgaga    3000
tcacagaagg caagaacccg gacgtgctga cggttcaccc cgattacttt ttgatcgatc    3060
ccggcatcgg ccgttttctc taccgcctgg cacgccgcgc cgcaggcaag gcagaagcca    3120
gatggttgtt caagacgatc tacgaacgca gtggcagcgc cggagagttc aagaagttct    3180
gtttcaccgt gcgcaagctg atcgggtcaa atgacctgcc ggagtacgat ttgaaggagg    3240
aggcggggca ggctggcccg atcctagtca tgcgctaccg caacctgatc gagggcgaag    3300
catccgccgg ttcctaatgt acggagcaga tgctagggca aattgccta gcaggggaaa    3360 aaggtcgaaa aggtctcttt cctgtggata gcacgtacat tgggaaccca aagccgtaca    3420
ttgggaaccg gaacccgtac attgggaacc caaagccgta cattgggaac cggtcacaca    3480
tgtaagtgac tgatataaaa gagaaaaaag gcgattttc cgcctaaaac tctttaaaac    3540
ttattaaaac tcttaaaacc cgcctggcct gtgcataact gtctggccag cgcacagccg    3600
```

-continued

```
aagagctgca aaaagcgcct acccttcggt cgctgcgctc cctacgcccc gccgcttcgc   3660
gtcggcctat cgcggccgct ggccgctcaa aaatggctgg cctacggcca ggcaatctac   3720
cagggcgcgg acaagccgcg ccgtcgccac tcgaccgccg gcgcccacat caaggcaccc   3780
tgcctcgcgc gtttcggtga tgacggtgaa aacctctgac acatgcagct cccggagacg   3840
gtcacagctt gtctgtaagc ggatgccggg agcagacaag cccgtcaggg gcgtcagcg    3900 ggtgttggcg ggtgtcgggg cgcagccatg acccagtcac gtagcgatag cggagtgtat   3960
actggcttaa ctatgcggca tcagagcaga ttgtactgag agtgcaccat atgcggtgtg   4020
aaataccgca cagatgcgta aggagaaaat accgcatcag gcgctcttcc gcttcctcgc   4080
tcactgactc gctgcgctcg gtcgttcggc tgcggcgagc ggtatcagct cactcaaagg   4140
cggtaatacg gttatccaca gaatcagggg ataacgcagg aaagaacatg tgagcaaaag   4200
gccagcaaaa ggccaggaac cgtaaaaagg ccgcgttgct ggcgtttttc cataggctcc   4260
gcccccctga cgagcatcac aaaaatcgac gctcaagtca gaggtggcga acccgacag    4320 gactataaag ataccaggcg tttccccctg gaagctccct cgtgcgctct cctgttccga   4380
ccctgccgct taccggatac ctgtccgcct ttctcccttc gggaagcgtg gcgctttctc   4440
atagctcacg ctgtaggtat ctcagttcgg tgtaggtcgt tcgctccaag ctgggctgtg   4500
tgcacgaacc ccccgttcag cccgaccgct gcgccttatc cggtaactat cgtcttgagt   4560
ccaacccggt aagacacgac ttatcgccac tggcagcagc cactggtaac aggattagca   4620
gagcgaggta tgtaggcggt gctacagagt tcttgaagtg gtggcctaac tacggctaca   4680
ctagaaggac agtatttggt atctgcgctc tgctgaagcc agttaccttc ggaaaaagag   4740
ttggtagctc ttgatccggc aaacaaacca ccgctggtag cggtggtttt tttgtttgca   4800
agcagcagat tacgcgcaga aaaaaaggat ctcaagaaga tcctttgatc ttttctacgg   4860
ggtctgacgc tcagtggaac gaaaactcac gttaagggat tttggtcatg catgatatat   4920
ctcccaattt gtgtagggct tattatgcac gcttaaaaat aataaaagca gacttgacct   4980
gatagtttgg ctgtgagcaa ttatgtgctt agtgcatcta atcgcttgag ttaacgccgg   5040
cgaagcggcg tcggcttgaa cgaatttcta gctagacatt atttgccgac taccttggtg   5100
atctcgcctt tcacgtagtg gacaaattct tccaactgat ctgcgcgcga ggccaagcga   5160
tcttcttctt gtccaagata agcctgtcta gcttcaagta tgacgggctg atactgggcc   5220
ggcaggcgct ccattgccca gtcggcagcg acatccttcg gcgcgatttt gccggttact   5280
gcgctgtacc aaatgcggga caacgtaagc actacatttc gctcatcgcc agcccagtcg   5340
ggcggcgagt tccatagcgt taaggtttca tttagcgcct caaatagatc ctgttcagga   5400
accggatcaa agagttcctc cgccgctgga cctaccaagg caacgctatg ttctcttgct   5460
tttgtcagca agatagccag atcaatgtcg atcgtggctg gctcgaagat acctgcaaga   5520
atgtcattgc gctgccattc tccaaattgc agttcgcgct tagctggata acgccacgga   5580
atgatgtcgt cgtgcacaac aatggtgact tctacagcgc ggagaatctc gctctctcca   5640
ggggaagccg aagtttccaa aaggtcgttg atcaaagctc gccgcgttgt ttcatcaagc   5700
cttacggtca ccgtaaccag caaatcaata tcactgtgtg gcttcaggcc gccatccact   5760
gcggagccgt acaaatgtac ggccagcaac gtcggttcga gatggcgctc gatgacgcca   5820
actacctctg atagttgagt cgatacttcg gcgatcaccg cttccccat gatgtttaac    5880 tttgttttag ggcgactgcc ctgctgcgta acatcgttgc tgctccataa catcaaacat   5940
cgacccacgg cgtaacgcgc ttgctgcttg gatgcccgag gcatagactg tacccaaaa    6000
```

-continued

```
aaacatgtca taacaagaag ccatgaaaac cgccactgcg ccgttaccac cgctgcgttc    6060
ggtcaaggtt ctggaccagt tgcgtgacgg cagttacgct acttgcatta cagcttacga    6120
accgaacgag gcttatgtcc actgggttcg tgcccgaatt gatcacaggc agcaacgctc    6180
tgtcatcgtt acaatcaaca tgctaccctc cgcgagatca tccgtgtttc aaacccggca    6240
gcttagttgc cgttcttccg aatagcatcg gtaacatgag caaagtctgc cgccttacaa    6300
cggctctccc gctgacgccg tcccggactg atgggctgcc tgtatcgagt ggtgattttg    6360
tgccgagctg ccggtcgggg agctgttggc tggctggtgg caggatatat tgtggtgtaa    6420
acaaattgac gcttagacaa cttaataaca cattgcggac gtttttaatg tactgaatta    6480
acgccgaatt gaattaattc ccatcttgaa agaaatatag tttaaatatt tattgataaa    6540
ataacaagtc aggtattata gtccaagcaa aaacataaat ttattgatgc aagtttaaat    6600
tcagaaatat ttcaataact gattatatca gctggtacat tgccgtagat gaaagactga    6660
gtgcgatatt atgtgtaata cataaattga tgatatagct agcttagctc atcgggggat    6720
ccgtcgaagc tagcttgggt cccgctcaga agaactcgtc aagaaggcga tagaaggcga    6780
tgcgctgcga atcgggagcg gcgataccgt aaagcacgag gaagcggtca gcccattcgc    6840
cgccaagctc ttcagcaata tcacgggtag ccaacgctat gtcctgatag cggtccgcca    6900
cacccagccg gccacagtcg atgaatccag aaaagcggcc attttccacc atgatattcg    6960
gcaagcaggc atcgccatgg gtcacgacga gatcctcgcc gtcgggcatg cgcgccttga    7020
gcctggcgaa cagttcggct ggcgcgagcc cctgatgctc ttcgtccaga tcatcctgat    7080
cgacaagacc ggcttccatc cgagtacgtg ctcgctcgat gcgatgtttc gcttggtggt    7140
cgaatgggca ggtagccgga tcaagcgtat gcagccgccg cattgcatca gccatgatgg    7200
atactttctc ggcaggagca aggtgagatg acaggagatc ctgccccggc acttcgccca    7260
atagcagcca gtcccttccc gcttcagtga caacgtcgag cacagctgcg caaggaacgc    7320
ccgtcgtggc cagccacgat agccgcgctg cctcgtcctg cagttcattc agggcaccgg    7380
acaggtcggt cttgacaaaa agaaccgggc gcccctgcgc tgacagccgg aacacggcgg    7440
catcagagca gccgattgtc tgttgtgccc agtcatagcc gaatagcctc tccacccaag    7500
cggccggaga acctgcgtgc aatccatctt gttcaatcca agctcccatg atcaaaactt    7560
acaaatttct ctgaacttgt atcctcagta cttcaaagaa aatagcttac accaaatttt    7620
ttcttgtttt cacaaatgcc gaacttggtt ccttatatag gaaaactcaa gggcaaaaat    7680
gacacgaaaa aatataaaag gataagtagt gggggataag attcctttgt gataaggtta    7740
ctttccgccc ttacattttc caccttacat gtgtcctcta tgtctctttc acaatcaccg    7800 acctatctt cttcttttca ttgttgtcgt cagtgcttac gtcttcaaga ttcttttctt    7860
cgcctggttc ttctttttca atttctacgt attcttcttc gtattctggc agtataggat    7920
cttgtatctg tacattcttc attttgaac ataggttgca tatgtgccgc atattgatct    7980
gcttcttgct gagctcacat aatacttcca tagttttccc cgtaaacatt ggattcttga    8040
tgctacatct tggataatta ccttctgtta ccaaggttat cccatcgaat tcgagctcgg    8100
tacccgggga tcctctagat ctgtcgacct gcaggcatgc aagcttagct tgagcttgga    8160
tcagattgtc gtttcccgcc ttcagtttaa actatcagtg tttgacagga tatattggcg    8220
ggtaaaccta agagaaaaga gcgtttatta gaataacgga tatttaaaag ggcgtgaaaa    8280
ggtttatccg ttcgtccatt tgtatgtgca tgccaaccac agggttcccc tcgggatcaa    8340
```

IDENTIFICATION AND CHARACTERIZATION OF A PAGODA PHENOTYPE (PGD) IN PLANTS

This application claims benefit of Ser. No. 60/201,329 filed May 2, 2000.

FIELD OF THE INVENTION

The present invention relates to a plant phenotype, designated PAGODA (PGD), together with DNA and polypeptide sequences associated with the same.

BACKGROUND OF THE INVENTION

The traditional methods for gene discovery, including chemical mutagenesis, irradiation and T-DNA insertion, used to screen loss of function mutants have limitations. Mutagenic methods such as these rarely identify genes that are redundant in the genome, and gene characterization is time-consuming and laborious.

Activation tagging is a method by which genes are randomly and strongly up-regulated on a genome-wide scale, after which specific phenotypes are screened for and selected. Isolation of mutants by activation tagging has been reported (Hayashi et al., 1992). An activation T-DNA tagging construct was used to activate genes in tobacco cell culture allowing the cells to grow in the absence of plant growth hormones (Walden et al., 1994). Genes have been isolated from plant genomic sequences flanking the T-DNA tag and putatively assigned to plant growth hormone responses. (See, e.g., Miklashevichs et al. 1997, Harling et al., 1997; Walden et. al., 1994; and Schell et al., 1998, which discusses related studies.)

The first gene characterized in Arabidopsis using activation tagging was a gene encoding the histone kinase involved in the cytokinin signal transduction pathway. The gene sequence was isolated from plant genomic DNA by plasmid rescue and the role of the gene, CKI1, in cytokinin responses in plants was confirmed by re-introduction into Arabidopsis (Kakimoto, 1996). This was followed by reports of several dominant mutants such as TINY, LHY and SHI using a similar approach along with the Ds transposable element (Wilson et al., 1996, Schaffer et al., 1998, Fridborg et al., 1999). In a more recent report, activation T-DNA tagging and screening plants for an early flowering phenotype led to the isolation of the FT gene (Kardailsky et al., 1999).

The potential application of activation tagging as a high through put technology for gene discovery has been demonstrated based on screening of several dominant mutant genes involved in photoreceptor, brassinosteroid, gibberellin and flowering signal pathways, as well as disease resistance. (See, e.g., Weigel et al., 2000, Christensen et al., 1998; Kardailsky et al., 1999).

SUMMARY OF THE INVENTION.

The invention provides nucleic acid and amino acid sequences associated with the PAGODA ("PGD") phenotype in plants, identified for its compact stature, curled leaves, and downward-oriented flowers/siliques relative to wild-type Arabidopsis plants.

In one aspect, the invention provides one or more isolated PGD nucleic acid sequences comprising a nucleic acid sequence that encodes or is complementary to a sequence that encodes a PGD polypeptide having at least 70%, 80%, 90% or more sequence identity to the amino acid sequence presented as SEQ ID NO:2.

In another aspect, the polynucleotide comprises a nucleic acid sequence that hybridizes, under high, medium, or low stringency conditions to the nucleic acid sequence, or fragment thereof, presented as SEQ ID NO:1, or the complement thereof.

In a related aspect, expression of one or more of such PGD polynucleotides in a plant is associated with the PGD phenotype.

The invention further provides plant transformation vectors, plant cells, plant parts and plants comprising a PGD nucleic acid sequence.

Expression of such a PGD nucleic acid sequence in a plant is associated with the PGD phenotype, presented as altered stature and leaf and floral organ morphology relative to the wild type plant.

The expression of a PGD nucleic acid sequence may be modified in ornamental plants, fruit and vegetable-producing plants, grain-producing plants, oil-producing plants and nut-producing plants, as well as other crop plants, resulting in the PGD phenotype.

In a further aspect the invention provides a method of modifying the stature and leaf and floral organ morphology in a plant by introducing a PGD nucleic acid sequence into plant progenitor cells and growing the cells to produce a transgenic plant.

DETAILED DESCRIPTION OF THE INVENTION

I. Definitions

Unless otherwise indicated, all technical and scientific terms used herein have the same meaning as they would to one skilled in the art of the present invention. Practitioners are particularly directed to Sambrook et al., 1989, and Ausubel FM et al., 1993, for definitions and terms of the art. It is to be understood that this invention is not limited to the particular methodology, protocols, and reagents described, as these may vary.

All publications cited herein, and listed below immediately after the examples, are expressly incorporated herein by reference for the purpose of describing and disclosing compositions and methodologies that might be used in connection with the invention.

As used herein, the term "vector" refers to a nucleic acid construct designed for transfer between different host cells. An "expression vector" refers to a vector that has the ability to incorporate and express heterologous DNA fragments in a foreign cell. Many prokaryotic and eukaryotic expression vectors are commercially available. Selection of appropriate expression vectors is within the knowledge of those having skill in the art.

A "heterologous" nucleic acid construct or sequence has a portion of the sequence which is not native to the plant cell in which it is expressed. Heterologous, with respect to a control sequence refers to a control sequence (i.e. promoter or enhancer) that does not function in nature to regulate the same gene the expression of which it is currently regulating. Generally, heterologous nucleic acid sequences are not endogenous to the cell or part of the genome in which they are present, and have been added to the cell, by infection, transfection, microinjection, electroporation, or the like. A "heterologous" nucleic acid construct may contain a control sequence/DNA coding sequence combination that is the same as, or different from a control sequence/DNA coding sequence combination found in the native plant.

As used herein, the term "gene" means the segment of DNA involved in producing a polypeptide chain, which may or may not include regions preceding and following the coding region, e.g. 5 ' untranslated (5' UTR) or "leader" sequences and 3' UTR or "trailer" sequences, as well as intervening sequences (introns) between individual coding segments (exons).

As used herein, "percent (%) sequence identity" with respect to a subject sequence, or a specified portion of a subject sequence, is defined as the percentage of nucleotides or amino acids in the candidate derivative sequence identical with the nucleotides or amino acids in the subject sequence (or specified portion thereof), after aligning the sequences and introducing gaps, if necessary to achieve the maximum percent sequence identity, as generated by the program WU-BLAST-2.0al9 (Altschul et al., J. Mol. Biol. (1997) 215:403–410; blast.wustl.edu/blast/README.html website) with all the search parameters set to default values. The HSP S and HSP S2 parameters are dynamic values and are established by the program itself depending upon the composition of the particular sequence and composition of the particular database against which the sequence of interest is being searched. A % identity value is determined by the number of matching identical nucleotides or amino acids divided by the sequence length for which the percent identity is being reported. "Percent (%) amino acid sequence similarity" is determined by doing the same calculation as for determining % amino acid sequence identity, but including conservative amino acid substitutions in addition to identical amino acids in the computation.

The term "% homology" is used interchangeably herein with the term "% identity."

A nucleic acid sequence is considered to be "selectively hybridizable" to a reference nucleic acid sequence if the two sequences specifically hybridize to one another under moderate to high stringency hybridization and wash conditions. Hybridization conditions are based on the melting temperature (Tm) of the nucleic acid binding complex or probe. For example, "maximum stringency" typically occurs at about Tm-5° C. (5° below the Tm of the probe); "high stringency" at about 5–10° below the Tm; "intermediate stringency" at about 10–20° below the Tm of the probe; and "low stringency" at about 20–25° below the Tm. Functionally, maximum stringency conditions may be used to identify sequences having strict identity or near-strict identity with the hybridization probe; while high stringency conditions are used to identify sequences having about 80% or more sequence identity with the probe.

Moderate and high stringency hybridization conditions are well known in the art (see, for example, Sambrook, et al, 1989, Chapters 9 and 11, and in Ausubel, F. M., et al., 1993, expressly incorporated by reference herein). An example of high stringency conditions includes hybridization at about 42° C. in 50% formamide, 5×SSC, 5×Denhardt's solution, 0.5% SDS and 100 µg/ml denatured carrier DNA followed by washing two times in 2×SSC and 0.5% SDS at room temperature and two additional times in 0.1×SSC and 0.5% SDS at 42° C.

As used herein, "recombinant" includes reference to a cell or vector, that has been modified by the introduction of a heterologous nucleic acid sequence or that the cell is derived from a cell so modified. Thus, for example, recombinant cells express genes that are not found in identical form within the native (non-recombinant) form of the cell or express native genes that are otherwise abnormally expressed, under expressed or not expressed at all as a result of deliberate human intervention.

As used herein, the terms "transformed", "stably transformed" or "transgenic" with reference to a plant cell means the plant cell has a non-native (heterologous) nucleic acid sequence integrated into its genome which is maintained through two or more generations.

As used herein, the term "expression" refers to the process by which a polypeptide is produced based on the nucleic acid sequence of a gene. The process includes both transcription and translation.

The term "introduced" in the context of inserting a nucleic acid sequence into a cell, means "transfection", or "transformation" or "transduction" and includes reference to the incorporation of a nucleic acid sequence into a eukaryotic or prokaryotic cell where the nucleic acid sequence may be incorporated into the genome of the cell (for example, chromosome, plasmid, plastid, or mitochondrial DNA), converted into an autonomous replicon, or transiently expressed (for example, transfected mRNA).

As used herein, a "plant cell" refers to any cell derived from a plant, including cells from undifferentiated tissue (e.g., callus) as well as plant seeds, pollen, progagules and embryos.

As used herein, the terms "native" and "wild-type" relative to a given plant trait or phenotype refers to the form in which that trait or phenotype is found in the same variety of plant in nature.

As used herein, the term "modified" regarding a plant trait, refers to a change in the phenotype of a transgenic plant relative to a non-transgenic plant, as it is found in nature.

As used herein, the term "$T_1$" refers to the generation of plants from the seed of $T_0$ plants. The $T_1$ generation is the first set of transformed plants that can be selected by application of a selection agent, e.g., an antibiotic or herbicide, for which the transgenic plant contains the corresponding resistance gene.

As used herein, the term "$T_2$" refers to the generation of plants by self-fertilization of the flowers of $T_1$ plants, previously selected as being transgenic.

As used herein, the term "plant part" includes any plant organ or tissue including, without limitation, seeds, embryos, meristematic regions, callus tissue, leaves, roots, shoots, gametophytes, sporophytes, pollen, and microspores. Plant cells can be obtained from any plant organ or tissue and cultures prepared therefrom. The class of plants which can be used in the methods of the present invention is generally as broad as the class of higher plants amenable to transformation techniques, including both monocotyledenous and dicotyledenous plants.

As used herein, "transgenic plant" includes reference to a plant that comprises within its genome a heterologous polynucleotide. Generally, the heterologous polynucleotide is stably integrated within the genome such that the polynucleotide is passed on to successive generations. The heterologous polynucleotide may be integrated into the genome alone or as part of a recombinant expression cassette. "Transgenic" is used herein to include any cell, cell line, callus, tissue, plant part or plant, the genotype of which has been altered by the presence of heterologous nucleic acid including those transgenics initially so altered as well as those created by sexual crosses or asexual propagation from the initial transgenic.

Thus a plant having within its cells a heterologous polynucleotide is referred to herein as a "transgenic plant". The heterologous polynucleotide can be either stably integrated into the genome, or can be extra-chromosomal. Preferably, the polynucleotide of the present invention is stably integrated into the genome such that the polynucleotide is passed on to successive generations. The polynucleotide is integrated into the genome alone or as part of a recombinant expression cassette. "Transgenic" is used herein to include any cell, cell line, callus, tissue, plant part or plant, the genotype of which has been altered by the presence of heterologous nucleic acids including those transgenics initially so altered as well as those created by sexual crosses or asexual reproduction of the initial transgenics.

A plant cell, tissue, organ, or plant into which the recombinant DNA constructs containing the expression constructs have been introduced is considered "transformed", "transfected", or "transgenic". A transgenic or transformed cell or plant also includes progeny of the cell or plant and progeny produced from a breeding program employing such a transgenic plant as a parent in a cross and exhibiting an altered phenotype resulting from the presence of a recombinant nucleic acid sequence. Hence, a plant of the invention will include any plant which has a cell containing a construct with introduced nucleic acid sequences, regardless of whether the sequence was introduced into the directly through transformation means or introduced by generational transfer from a progenitor cell which originally received the construct by direct transformation.

The terms "PAGODA" and "PGD", as used herein encompass native PAGODA (PGD) nucleic acid and amino acid sequences, homologues, variants and fragments thereof.

An "isolated" PGD nucleic acid molecule is a PGD nucleic acid molecule that is identified and separated from at least one contaminant nucleic acid molecule with which it is ordinarily associated in the natural source of the PGD nucleic acid. An isolated PGD nucleic acid molecule is other than in the form or setting in which it is found in nature. However, an isolated PGD nucleic acid molecule includes PGD nucleic acid molecules contained in cells that ordinarily express PGD where, for example, the nucleic acid molecule is in a chromosomal location different from that of natural cells.

As used herein, the term "mutant" with reference to a polynucleotide sequence or gene differs from the corresponding wild type polynucleotide sequence or gene either in terms of sequence or expression, where the difference contributes to a modified plant phenotype or trait. Relative to a plant or plant line, the term "mutant" refers to a plant or plant line which has a modified plant phenotype or trait, where the modified phenotype or trait is associated with the modified expression of a wild type polynucleotide sequence or gene.

Generally, a "variant" polynucleotide sequence encodes a "variant" amino acid sequence which is altered by one or more amino acids from the reference polypeptide sequence. The variant polynucleotide sequence may encode a variant amino acid sequence having "conservative" or "non-conservative" substitutions. Variant polynucleotides may also encode variant amino acid sequences having amino acid insertions or deletions, or both.

As used herein, the term "phenotype" may be used interchangeably with the term "trait". The terms refer to a plant characteristic which is readily observable or measurable and results from the interaction of the genetic make-up of the plant with the environment in which it develops. Such a phenotype includes chemical changes in the plant make-up resulting from enhanced gene expression which may or may not result in morphological changes in the plant, but which are measurable using analytical techniques known to those of skill in the art.

As used herein, the term "interesting phenotype" with reference to a plant produced by the methods described herein refers to a readily observable or measurable phenotype demonstrated by a $T_1$ and/or subsequent generation plant, which is not displayed by a plant that has not been so transformed (and/or is not the progeny of a plant that has been so transformed) and represents an improvement in the plant. An "improvement" is a feature that may enhance the utility of a plant species or variety by providing the plant with a unique quality. By unique quality is meant a novel feature or a change to an existing feature of the plant species which is a quantitative change (increase or decrease) or a qualitative change in a given feature or trait.

II. The Identified PGD Phenotype and Gene

The gene and phenotype of this invention were identified in a large-scale screen using activation tagging. Activation tagging is a process by which a heterologous nucleic acid construct comprising a nucleic acid control sequence, e.g. an enhancer, is inserted into a plant genome. The enhancer sequences act to enhance transcription of a one or more native plant genes (See, e.g., Walden R, et al., 1994; Weigel D et al. 2000).

Briefly, a large number of Arabidopsis plants were transformed with the activation tagging vector pSKI015 (Weigel et al, 2000), which comprises a T-DNA (i.e., the sequence derived from the Ti plasmid of Agrobacterium tumifaciens that are transferred to a plant cell host during Agrobacterium infection), an enhancer element and a selectable marker gene. Following random insertion of pSKI015 into the genome of transformed plants, the enhancer element can result in up-regulation genes in the vicinity of the T-DNA insertion, generally within 5–10 kilobase (kb) of the insertion. In the $T_1$ generation, plants were exposed to the selective agent in order to specifically recover those plants that expressed the selectable marker and therefore harbored insertions of the activation-tagging vector. Transformed plants were observed for interesting phenotypes, which are generally identified at the $T_1$, $T_2$ and/or $T_3$ generations. Interesting phenotypes may be identified based on morphology, a biochemical screen, herbicide tolerance testing, herbicide target identification, fungal or bacterial resistance testing, insect or nematode resistance testing, screening for stress tolerance, such as drought, salt or antibiotic tolerance, and output traits, such as oil, starch, pigment, or vitamin composition. Genomic sequence surrounding the T-DNA insertion is analyzed in order to identify genes responsible for the interesting phenotypes. Genes responsible for causing such phenotypes are identified as attractive targets for manipulation for agriculture, food, ornamental plant, and/or pharmaceutical industries.

It will be appreciated that in most cases when a modified phenotype results from the enhanced expression of a tagged gene, the phenotype is dominant. In some cases, the enhanced expression of a given native plant gene or a fragment thereof may result in decreased expression or inactivation of its homologue or another native plant gene, which results in the interesting phenotype. The T-DNA insertion may also result in disruption ("loss-of-function") of a native plant gene, in which case the phenotype is generally recessive.

The present invention provides a morphological phenotype, identified in Arabidopsis where $T_1$, $T_2$, and $T_3$ plants were observed as having a compact stature with curled leaves and downward-oriented ("brevi-pedicel" or "basi-petal") flowers/siliques, which is referred to as the PGD phenotype.

The invention also provides a newly identified and isolated nucleic acid sequence that was identified by analysis of the genomic DNA sequence surrounding the T-DNA insertion correlating with the PGD phenotype. In particular, applicants have identified and characterized the open reading frame of the PGD gene, which is specifically overexpressed in plants having the PGD phenotype, and which is provided in SEQ ID NO:1. A detailed description of the isolation and characterization of PGD is set forth in the Examples.

III. Compositions of the Invention

A. PGD Nucleic Acids

The PGD gene may be used in the development of transgenic plants having a desired phenotype. This may be accomplished using the native PGD sequence, a variant PGD sequence or a homologue or fragment thereof.

A PGD nucleic acid sequence of this invention may be a DNA or RNA sequence, derived from genomic DNA, cDNA or mRNA. The nucleic acid sequence may be cloned, for example, by isolating genomic DNA from an appropriate source, and amplifying and cloning the sequence of interest using PCR. Alternatively, nucleic acid sequence may be synthesized, either completely or in part, especially where it is desirable to provide plant-preferred sequences. Thus, all or a portion of the desired structural gene (that portion of the gene which encodes a polypeptide or protein) may be synthesized using codons preferred by a selected host.

The invention provides a polynucleotide comprising a nucleic acid sequence which encodes or is complementary to a sequence which encodes a PGD polypeptide having the amino acid sequence presented in SEQ ID NO:2 and a polynucleotide sequence identical over its entire length to the PGD nucleic acid sequence presented SEQ ID NO:1. The invention also provides the coding sequence for the mature PGD polypeptide, a variant or fragment thereof, as well as the coding sequence for the mature polypeptide or a fragment thereof in a reading frame with other coding sequences, such as those encoding a leader or secretory sequence, a pre-, pro-, or prepro- protein sequence.

A PGD polynucleotide can also include non-coding sequences, including for example, but not limited to, non-coding 5' and 3' sequences, such as the transcribed, untranslated sequences, termination signals, ribosome binding sites, sequences that stabilize mRNA, introns, polyadenylation signals, and additional coding sequence that encodes additional amino acids. For example, a marker sequence can be included to facilitate the purification of the fused polypeptide. Polynucleotides of the present invention also include polynucleotides comprising a structural gene and the naturally associated sequences that control gene expression.

When an isolated polynucleotide of the invention comprises a PGD nucleic acid sequence flanked by non-PGD nucleic acid sequence, the total length of the combined polynucleotide is typically less than 25 kb, and usually less than 20 kb, or 15 kb, and in some cases less than 10 kb, or 5 kb.

In addition to the PGD nucleic acid and corresponding polypeptide sequences described herein, it is contemplated that PGD variants can be prepared. PGD variants can be prepared by introducing appropriate nucleotide changes into the PGD nucleic acid sequence; by synthesis of the desired PGD polypeptide or by altering the expression level of the PGD gene in plants. Those skilled in the art will appreciate that amino acid changes may alter post-translational processing of the PGD polypeptide, such as changing the number or position of glycosylation sites or altering the membrane anchoring characteristics.

In one aspect, preferred PGD coding sequences include a polynucleotide comprising a nucleic acid sequence which encodes or is complementary to a sequence which encodes a PGD polypeptide having at least 50%, 60%, 70%, 75%, 80%, 85%, 90%, 95% or more sequence identity to the amino acid sequence presented in SEQ ID NO:2.

In another aspect, preferred variants include a PGD polynucleotide sequence that is at least 50% to 60% identical over its entire length to the PGD nucleic acid sequence presented as SEQ ID NO:1, and nucleic acid sequences that are complementary to such a PGD sequence. More preferable are PGD polynucleotide sequences comprise a region having at least 70%, 80%, 85%, 90% or 95% or more sequence identity to the PGD sequence presented as SEQ ID NO:1.

In a related aspect, preferred variants include polynucleotides that are be "selectively hybridizable" to the PGD polynucleotide sequence presented as SEQ ID NO:1.

Sequence variants also include nucleic acid molecules that encode the same polypeptide as encoded by the PGD polynucleotide sequence described herein. Thus, where the coding frame of an identified nucleic acid molecules is known, for example by homology to known genes or by extension of the sequence, it is appreciated that as a result of the degeneracy of the genetic code, a number of coding sequences can be produced. For example, the triplet CGT encodes the amino acid arginine. Arginine is alternatively encoded by CGA, CGC, CGG, AGA, and AGG. Therefore it is appreciated that such substitutions in the coding region fall within the sequence variants that are covered by the present invention. Any and all of these sequence variants can be utilized in the same way as described herein for the identified PGD parent sequence, SEQ ID NO:1.

It is further appreciated that such sequence variants may or may not selectively hybridize to the parent sequence. This would be possible, for example, when the sequence variant includes a different codon for each of the amino acids encoded by the parent nucleotide. Such variants are, nonetheless, specifically contemplated and encompassed by the present invention. In accordance with the present invention, also encompassed are sequences that at least 70% identical to such degeneracy-derived sequence variants.

Although PGD nucleotide sequence variants are preferably capable of hybridizing to the nucleotide sequences recited herein under conditions of moderately high or high stringency, there are, in some situations, advantages to using variants based on the degeneracy of the code, as described above. For example, codons may be selected to increase the rate at which expression of the peptide occurs in a particular prokaryotic or eukaryotic organism, in accordance with the optimum codon usage dictated by the particular host organism. Alternatively, it may be desirable to produce RNA having longer half lives than the mRNA produced by the recited sequences.

Variations in the native full-length PGD nucleic acid sequence described herein, may be made, for example, using any of the techniques and guidelines for conservative and non-conservative mutations, as generally known in the art, oligonucleotide-mediated (site-directed) mutagenesis, alanine scanning, and PCR mutagenesis. Site-directed mutagenesis (Kunkel T A et al., 1991); cassette mutagenesis (Crameri A et al., 1995); restriction selection mutagenesis (Haught C et al., 1994), or other known techniques can be performed on the cloned DNA to produce nucleic acid sequences encoding PGD variants.

It is contemplated that the gene sequences associated with the PGD phenotype may be synthesized, either completely or in part, especially where it is desirable to provide host-preferred sequences. Thus, all or a portion of the desired structural gene (that portion of the gene which encodes the protein) may be synthesized using codons preferred by a selected host. Host-preferred codons may be determined, for example, from the codons used most frequently in the proteins expressed in a desired host species.

It is preferred that a PGD polynucleotide encodes a PGD polypeptide that retains substantially the same biological function or activity as the mature PGD polypeptide encoded by the polynucleotide set forth as SEQ ID NO:1 (i.e. results in a PGD phenotype when overexpressed in a plant).

Variants also include fragments of the PGD polynucleotide of the invention, which can be used to synthesize a full-length PGD polynucleotide. Preferred embodiments include polynucleotides encoding polypeptide variants wherein 5 to 10, 1 to 5, 1 to 3, 2, 1 or no amino acid residues of a PGD polypeptide sequence of the invention are substituted, added or deleted, in any combination. Particularly preferred are substitutions, additions, and deletions that are silent such that they do not alter the properties or activities of the polynucleotide or polypeptide.

A nucleotide sequence encoding a PGD polypeptide can also be used to construct hybridization probes for further genetic analysis. Screening of a cDNA or genomic library with the selected probe may be conducted using standard procedures, such as described in Sambrook et al., 1989). Hybridization conditions, including moderate stringency and high stringency, are provided in Sambrook et al., supra.

The probes or portions thereof may also be employed in PCR techniques to generate a pool of sequences for identification of closely related PGD sequences. When PGD sequences are intended for use as probes, a particular portion of a PGD encoding sequence, for example a highly conserved portion of the coding sequence may be used.

For example, a PGD nucleotide sequence may be used as a hybridization probe for a cDNA library to isolate genes, for example, those encoding naturally-occurring variants of PGD from other plant species, which have a desired level of sequence identity to the PGD nucleotide sequence disclosed in SEQ ID NO:1. Exemplary probes have a length of about 20 to about 50 bases.

In another exemplary approach, a nucleic acid encoding a PGD polypeptide may be obtained by screening selected cDNA or genomic libraries using the deduced amino acid sequence disclosed herein, and, if necessary, using conventional primer extension procedures as described in Sambrook et al., supra, to detect PGD precursors and processing intermediates of mRNA that may not have been reverse-transcribed into cDNA.

As discussed above, nucleic acid sequences of this invention may include genomic, cDNA or mRNA sequence. By "encoding" is meant that the sequence corresponds to a particular amino acid sequence either in a sense or anti-sense orientation. By "extrachromosomal" is meant that the sequence is outside of the plant genome of which it is naturally associated. By "recombinant" is meant that the sequence contains a genetically engineered modification through manipulation via mutagenesis, restriction enzymes, and the like.

Once the desired form of a PGD nucleic acid sequence, homologue, variant or fragment thereof, is obtained, it may be modified in a variety of ways. Where the sequence involves non-coding flanking regions, the flanking regions may be subjected to resection, mutagenesis, etc. Thus, transitions, transversions, deletions, and insertions may be performed on the naturally occurring sequence.

With or without such modification, the desired form of the PGD nucleic acid sequence, homologue, variant or fragment thereof, may be incorporated into a plant expression vector for transformation of plant cells.

B. PGD Polypeptides

In one preferred embodiment, the invention provides a PGD polypeptide, having a native mature or full-length PGD polypeptide sequence comprising the sequence presented in SEQ ID NO:2. A PGD polypeptide of the invention can be the mature PGD polypeptide, part of a fusion protein or a fragment or variant of the PGD polypeptide sequence presented in SEQ ID NO:2.

Ordinarily, a PGD polypeptide of the invention has at least 50% to 60% identity to a PGD amino acid sequence over its entire length. More preferable are PGD polypeptide sequences that comprise a region having at least 70%, 80%, 85%, 90% or 95% or more sequence identity to the PGD polypeptide sequence of SEQ ID NO:2.

Fragments and variants of the PGD polypeptide sequence of SEQ ID NO:2, are also considered to be a part of the invention. A fragment is a variant polypeptide that has an amino acid sequence that is entirely the same as part but not all of the amino acid sequence of the previously described polypeptides. Exemplary fragments comprises at least 10, 20, 30, 40, 50, 75, or 100 contiguous amino acids of SEQ ID NO:2. The fragments can be "free-standing" or comprised within a larger polypeptide of which the fragment forms a part or a region, most preferably as a single continuous region. Preferred fragments are biologically active fragments, which are those fragments that mediate activities of the polypeptides of the invention, including those with similar activity or improved activity or with a decreased activity. Also included are those fragments that antigenic or immunogenic in an animal, particularly a human.

PGD polypeptides of the invention also include polypeptides that vary from the PGD polypeptide sequence of SEQ ID NO:2. These variants may be substitutional, insertional or deletional variants. The variants typically exhibit the same qualitative biological activity as the naturally occurring analogue, although variants can also be selected which have modified characteristics as further described below.

A "substitution" results from the replacement of one or more nucleotides or amino acids by different nucleotides or amino acids, respectively.

An "insertion" or "addition" is that change in a nucleotide or amino acid sequence which has resulted in the addition of one or more nucleotides or amino acid residues, respectively, as compared to the naturally occurring sequence.

A "deletion" is defined as a change in either nucleotide or amino acid sequence in which one or more nucleotides or amino acid residues, respectively, are absent.

Amino acid substitutions are typically of single residues; insertions usually will be on the order of from about 1 to 20 amino acids, although considerably larger insertions may be tolerated. Deletions range from about 1 to about 20 residues, although in some cases deletions may be much larger.

Substitutions, deletions, insertions or any combination thereof may be used to arrive at a final derivative. Generally these changes are done on a few amino acids to minimize the alteration of the molecule. However, larger changes may be tolerated in certain circumstances.

Amino acid substitutions can be the result of replacing one amino acid with another amino acid having similar structural and/or chemical properties, such as the replacement of a leucine with a serine, i.e., conservative amino acid replacements. Insertions or deletions may optionally be in the range of 1 to 5 amino acids.

Substitutions are generally made in accordance with known "conservative substitutions". A "conservative substitution" refers to the substitution of an amino acid in one class by an amino acid in the same class, where a class is defined by common physicochemical amino acid side chain properties and high substitution frequencies in homologous proteins found in nature (as determined, e.g., by a standard Dayhoff frequency exchange matrix or BLOSUM matrix). (See generally, Doolittle, R. F., 1986.)

A "non-conservative substitution" refers to the substitution of an amino acid in one class with an amino acid from another class.

PGD polypeptide variants typically exhibit the same qualitative biological activity as the naturally occurring analogue, although variants also are selected to modify the characteristics of the PGD polypeptide, as needed. For example, glycosylation sites, and more particularly one or more O-linked or N-linked glycosylation sites may be altered or removed. Those skilled in the art will appreciate that amino acid changes may alter post-translational processes of the PGD polypeptide, such as changing the number or position of glycosylation sites or altering the membrane anchoring characteristics.

The variations can be made using methods known in the art such as oligonucleotide-mediated (site-directed) mutagenesis, alanine scanning, and PCR mutagenesis. Site-directed mutagenesis [Carter et al., 1986; Zoller et al., 1987], cassette mutagenesis [Wells et al., 1985], restriction selection mutagenesis [Wells et al., 1986] or other known techniques can be performed on the cloned DNA to produce the PGD polypeptide-encoding variant DNA.

Also included within the definition of PGD polypeptides are other related PGD polypeptides. Thus, probe or degenerate PCR primer sequences may be used to find other related polypeptides. Useful probe or primer sequences may be designed to all or part of the PGD polypeptide sequence, or to sequences outside the coding region. As is generally known in the art, preferred PCR primers are from about 15 to about 35 nucleotides in length, with from about 20 to about 30 being preferred, and may contain inosine as needed. The conditions for the PCR reaction are generally known in the art.

Covalent modifications of PGD polypeptides are also included within the scope of this invention. For example, the invention provides PGD polypeptides that are a mature protein and may comprise additional amino or carboxyl-terminal amino acids, or amino acids within the mature polypeptide (for example, when the mature form of the protein has more than one polypeptide chain). Such sequences can, for example, play a role in the processing of a protein from a precursor to a mature form, allow protein transport, shorten or lengthen protein half-life, or facilitate manipulation of the protein in assays or production. It is contemplated that cellular enzymes can be used to remove any additional amino acids from the mature protein. [See, e.g., Creighton, T E, 1983].

In a preferred embodiment, overexpression of a PGD polypeptide or variant thereof is associated with the PGD phenotype.

C. Antibodies

The present invention further provides anti-PGD polypeptide antibodies. The antibodies may be polyclonal, monoclonal, humanized, bispecific or heteroconjugate antibodies.

Methods of preparing polyclonal antibodies are known to the skilled artisan. Such polyclonal antibodies can be produced in a mammal, for example, following one or more injections of an immunizing agent, and preferably, an adjuvant. Typically, the immunizing agent and/or adjuvant will be injected into the mammal by a series of subcutaneous or intraperitoneal injections. The immunizing agent may include a PGD polypeptide or a fusion protein thereof. It may be useful to conjugate the antigen to a protein known to be immunogenic in the mammal being immunized. The immunization protocol may be determined by one skilled in the art based on standard protocols or by routine experimentation.

Alternatively, the anti-PGD polypeptide antibodies may be monoclonal antibodies. Monoclonal antibodies may be produced by hybridomas, wherein a mouse, hamster, or other appropriate host animal, is immunized with an immunizing agent to elicit lymphocytes that produce or are capable of producing antibodies that will specifically bind to the immunizing agent [Kohler et al., 1975]. Monoclonal antibodies may also be made by recombinant DNA methods, such as those described in U.S. Pat. No. 4,816,567.

The anti-PGD polypeptide antibodies of the invention may further comprise humanized antibodies or human antibodies. The term "humanized antibody" refers to humanized forms of non-human (e.g., murine) antibodies that are chimeric antibodies, immunoglobulin chains or fragments thereof (such as Fv, Fab, Fab', $F(ab')_2$ or other antigen-binding partial sequences of antibodies) which contain some portion of the sequence derived from non-human antibody. Methods for humanizing non-human antibodies are well known in the art, as further detailed in Jones et al., 1986; Riechmann et al., 1988; and Verhoeyen et al., 1988. Methods for producing human antibodies are also known in the art. See, e.g., Jakobovits, A, et al., 1995; Jakobovits, A, 1995.

In one exemplary approach, anti-PGD polyclonal antibodies are used for gene isolation. Western blot analysis may be conducted to determine that PGD or a related protein is present in a crude extract of a particular plant species. When reactivity is observed, genes encoding the related protein may be isolated by screening expression libraries representing the particular plant species. Expression libraries can be constructed in a variety of commercially available vectors, including lambda gtl 1, as described in Sambrook, et al. , 1989.

IV. Utility Of the PGD Phenotype and Gene

From the foregoing, it can be appreciated that the PGD nucleotide sequence, protein sequence and phenotype find utility in modulated expression of the PGD protein and the development of non-native phenotypes associated with such modulated expression.

The PGD phenotype has features that distinguish the mutant from wild type Arabidopsis. The invention has application to ornamental plants and in the cut flower industry. For example, the phenotype could be applied to the well-known garden plants such as the wallflower (*Cherianthus cheiri*), Honesty and Aubretia of the Cruciferae family and to ornamental tobacco (*Nicotiana alata*) a solanaceous member and other ornamental plant species.

The degree of stem and inflorescence bending is one of the parameters of cut flower quality (Jong, J. de et al., *Acta Horticulturae*, 482: 287–290, 1999; Littlejohn and Blomerus, Genetic Resources and Crop Protection 44: 227–234, 1997).

In addition, the modulated expression of PGD could be used to change the branching architecture of trees that could have an impact on wood processing industry. In addition, the appressed pod (silique) feature could be applied to certain legumes for efficient pod set, prevention of early shattering of pods and may facilitate harvest, e.g., of Canola.

The observed morphology is one version of the phenotype. The expression of the PGD gene may be modulated with regard to the level of expression and also the tissue specificity of expression. For example: the pendulous trait could be expressed in the leaves at a desired angle so as to increase the photoreception area leading to increased photosynthate production. Such a modification is applicable to herbaceous crops/major cereal crops/legumes/trees.

In practicing the invention, the PGD phenotype and modified PGD expression is generally applicable to any type of plant The methods described herein are generally applicable to all plants. Although activation tagging and gene identification is carried out in Arabidopsis, following identification of a nucleic acid sequence and associated phenotype, the selected gene, a homologue, variant or fragment thereof, may be expressed in any type of plant. In one aspect, the invention is directed to fruit- and vegetable-bearing plants. In a related aspect, the invention is directed to the cut flower industry, grain-producing plants, oil-producing plants and nut-producing plants, as well as other crops including, but not limited to, cotton (Gossypium), alfalfa (Medicago sativa), flax (Linum usitatissimum), tobacco (Nicotiana), turfgrass (Poaceae family), and other forage crops.

The skilled artisan will recognize that a wide variety of transformation techniques exist in the art, and new techniques are continually becoming available. Any technique that is suitable for the target host plant can be employed within the scope of the present invention. For example, the constructs can be introduced in a variety of forms including, but not limited to as a strand of DNA, in a plasmid, or in an artificial chromosome. The introduction of the constructs into the target plant cells can be accomplished by a variety of techniques, including, but not limited to Agrobacterium-mediated transformation, electroporation, microinjection, microprojectile bombardment calcium-phosphate-DNA co-precipitation or liposome-mediated transformation of a heterologous nucleic acid construct comprising the PGD coding sequence. The transformation of the plant is preferably permanent, i.e. by integration of the introduced expression constructs into the host plant genome, so that the introduced constructs are passed onto successive plant generations.

In one embodiment, binary Ti-based vector systems may be used to transfer and confirm the association between enhanced expression of an identified gene with a particular plant trait or phenotype. Standard Agrobacterium binary vectors are known to those of skill in the art and many are commercially available, such as pBI121 (Clontech Laboratories, Palo Alto, Calif.).

The optimal procedure for transformation of plants with Agrobacterium vectors will vary with the type of plant being transformed. Exemplary methods for Agrobacterium-mediated transformation include transformation of explants of hypocotyl, shoot tip, stem or leaf tissue, derived from sterile seedlings and/or plantlets. Such transformed plants may be reproduced sexually, or by cell or tissue culture. Agrobacterium transformation has been previously described for a large number of different types of plants and methods for such transformation may be found in the scientific literature.

Depending upon the intended use, a heterologous nucleic acid construct may be made which comprises a nucleic acid sequence associated with the PGD phenotype, and which encodes the entire protein, or a biologically active portion thereof for transformation of plant cells and generation of transgenic plants.

The expression of a PGD nucleic acid sequence or a homologue, variant or fragment thereof may be carried out under the control of a constitutive, inducible or regulatable promoter. In some cases expression of the PGD nucleic acid sequence or homologue, variant or fragment thereof may regulated in a developmental stage or tissue-associated or tissue-specific manner. Accordingly, expression of the nucleic acid coding sequences described herein may be regulated with respect to the level of expression, the tissue type(s) where expression takes place and/or developmental stage of expression leading to a wide spectrum of applications wherein the expression of a PGD coding sequence is modulated in a plant.

Strong promoters with enhancers may result in a high level of expression. When a low level of basal activity is desired, a weak promoter may be a better choice. Expression of PGD nucleic acid sequence or homologue, variant or fragment thereof may also be controlled at the level of transcription, by the use of cell type specific promoters or promoter elements in the plant expression vector.

Numerous promoters useful for heterologous gene expression are available. Exemplary constitutive promoters include the raspberry E4 promoter (U.S. Pat. Nos. 5,783,393 and 5,783,394), the 35S CaMV (Jones J D et al, 1992), the CsVMV promoter (Verdaguer B et al., 1998) and the melon actin promoter. Exemplary tissue-specific promoters include the tomato E4 and E8 promoters (U.S. Pat. No. 5,859,330) and the tomato 2AII gene promoter (Van Haaren M J J et al., 1993).

When PGD sequences are intended for use as probes, a particular portion of a PGD encoding sequence, for example a highly conserved portion of a coding sequence may be used.

In yet another aspect, in some cases it may be desirable to inhibit the expression of endogenous PGD sequences in a host cell. Exemplary methods for practicing this aspect of the invention include, but are not limited to antisense suppression (Smith, et al.,1988); co-suppression (Napoli, et al.,1989); ribozymes (PCT Publication WO 97/10328); and combinations of sense and antisense (Waterhouse, et al., 1998). Methods for the suppression of endogenous sequences in a host cell typically employ the transcription or transcription and translation of at least a portion of the sequence to be suppressed. Such sequences may be homologous to coding as well as non-coding regions of the endogenous sequence. In some cases, it may be desirable to inhibit expression of the PGD nucleotide sequence. This may be accomplished using procedures generally employed by those of skill in the art together with the PGD nucleotide sequence provided herein.

Standard molecular and genetic tests may be performed to analyze the association between a cloned gene and an observed phenotype. A number of other techniques that are useful for determining (predicting or confirming) the function of a gene or gene product in plants are described below.

1. DNA/RNA Analysis

DNA taken form a mutant plant may be sequenced to identify the mutation at the nucleotide level. The mutant phenotype may be rescued by overexpressing the wild type (WT) gene. The stage- and tissue-specific gene expression patterns in mutant vs. WT lines, for instance, by in situ hybridization, may be determined. Analysis of the methylation status of the gene, especially flanking regulatory regions, may be performed. Other suitable techniques include overexpression, ectopic expression, expression in other plant species and gene knock-out (reverse genetics, targeted knock-out, viral induced gene silencing (VIGS, see Baulcombe D, 1999).

In a preferred application, microarray analysis, also known as expression profiling or transcript profiling, is used to simultaneously measure differences or induced changes in the expression of many different genes. Techniques for microarray analysis are well known in the art (Schena M et al., Science (1995) 270:467–470; Baldwin D et al., 1999; Dangond F, Physiol Genomics (2000) 2:53–58; van Hal NL et al., J Biotechnol (2000) 78:271–280; Richmond T and Somerville S, Curr Opin Plant Biol (2000) 3:108–116). Microarray analysis of individual tagged lines may be carried out, especially those from which genes have been isolated. Such analysis can identify other genes that are coordinately regulated as a consequence of the overexpression of the gene of interest, which may help to place an unknown gene in a particular pathway.

2. Gene Product Analysis

Analysis of gene products may include recombinant protein expression, antisera production, immunolocalization, biochemical assays for catalytic or other activity, analysis of phosphorylation status, and analysis of interaction with other proteins via yeast two-hybrid assays.

3. Pathway Analysis

Pathway analysis may include placing a gene or gene product within a particular biochemical or signaling pathway based on its overexpression phenotype or by sequence homology with related genes. Alternatively, analysis may comprise genetic crosses with WT lines and other mutant lines (creating double mutants) to order the gene in a pathway, or determining the effect of a mutation on expression of downstream "reporter" genes in a pathway.

4. Other Analyses

Other analyses may be performed to determine or confirm the participation of the isolated gene and its product in a particular metabolic or signaling pathway, and to help determine gene function.

All publications, patents and patent applications are herein expressly incorporated by reference in their entirety.

While the invention has been described with reference to specific methods and embodiments, it will be appreciated that various modifications and changes may be made without departing from the invention.

EXAMPLE 1

Generation of Plants with a PGD Phenotype by Transformation with an Activation Tagging Construct

A. Agrobacterium Vector Preparation

Mutants were generated using the activation tagging "ACTTAG" vector, pSKI015 (GenBank Identifier [GI] 6537289; Weigel D et al., 2000).).

Transformed *E. coli* colonies and cultures containing the pSKI015 activation tagging construct was confirmed by selection on media containing 100 µg/ml ampicillin. Agrobacterium colonies and cultures were grown in selective media containing 100 µg/ml carbenicillin. The presence of the pSKI015 construct was verified in colonies by PCR primers that span the ocs terminator in the BAR selection cassette under the following PCR conditions: 30 cycles of 94° C. 30 seconds; 63° C. 40 seconds; 72° C. 120 seconds.

For long-term storage, PCR-positive colonies were grown in selective media, glycerol added to a final concentration of 30% and cultures quick frozen then stored at −80° C. For the initiation of dense Agrobacterium cultures for plant transformation, stock cultures were grown in selective media, glycerol added to a final concentration of 30%, and a number of 20 µl aliquots quick frozen in liquid nitrogen and stored at −80° C.

pSKI015 was maintained in Agrobacterium GV3101 without the helper plasmid and in Agrobacterium strain EHA 105. An Agrobacterium culture was prepared by starting a 50 ml culture 4–5 days prior to plant transformation (e.g., by "dunking"). Liquid cultures were grown at 28° C., on an orbital shaker at 200 rpm, in LBB with Carbenicillin (Cb) at 100 mg/l to select for the plasmid, with 50 mg/l Kanamycin (Kan) added to select for the helper plasmid. After 2 days, this small culture was used to inoculate 6–8 liters (L) of LBB with Cb 100 mg/l and Kan 50 mg/l, IL each in 2000 ml Erlenmeyer flasks. Cultures are placed on a shaker for 2–3 days, checked for cell concentration by evaluating the $OD_{600}$ (visible light at 600 nm) using a spectrophotometer with an $OD_{600}$ reading for between 1.5–2.5 preferred. The cultures were then centrifuged at 4,500 RCF for 15 minutes at room temperature (18–22° C.), the bacteria resuspended to approximately $OD_{600}$=0.8 with about 500 ml per dunking vessel. Approximately 15–20 liters were prepared for 200 pots, and 20–30 plants dunked at a time.

B. Growth and Selection of *Arabidopsis thaliana* Plants

Arabidopsis plants were grown in Premier HP soil which contains peat moss and perlite, using a minimal amount of N-P-K (171-2-133) fertilizer diluted to 1/10 the strength, with sub-irrigation, as needed and a n 18 hr day length using natural light supplemented by high pressure sodium lamps at a temperature of 20–25° C. Seeds were sown under humidity domes for the first 4–7 days, then transferred to a greenhouse having approximately 70% humidity.

Healthy Arabidopsis plants were grown from wild type Arabidopsis seed, Ecotype: Col-0, under long days (16 hrs) in pots in soil covered with bridal veil or window screen, until they flowered.

Plants began flowering after about 3–4 weeks, with watering and fertilizing continued as needed until a majority of the siliques turned yellow/brown. Then plants were then left to dry out and seed collected by breaking open siliques to release the seed. Seed was stored at room temperature for a few days, then stored at 4° C. in an airtight container with desiccant.

Plants are monitored for pests and pathogens, particularly, fungus gnats, white flies, and aphids, with pest control applied as needed, e.g., application of Talstar and Azatin for whitefly, thrips and fungus gnats; application of Gnatrol for fungus gnats, biological control (e.g. mites, for gnat larvae) and safer soap.

Transformation was accomplished via a floral dip method wherein floral tissues were dipped into a solution containing Agrobacterium tumefaciens, 5% sucrose and a surfactant Silwet L-77, as described in Cough, SJ and Bent, AF, 1998.

Briefly, above-ground parts of 2,000–3,000 plants were dipped (dunked) into an Agrobacterium culture (GV3101 with pMP90RK, helper plasmid) carrying ACTTAG (binary plasmid pSKI.015), 2–3 days after clipping for 15 minutes, with gentle agitation, then placing plants on their sides under a humidity dome or cover for 16–24 hours to maintain high humidity.

A second dunking was carried out 6 days after removing the humidity domes, as described above. Plants were watered regularly until seeds were mature, at which time watering was stopped.

C. Selection Of Transgenic Plants

Dry $T_1$ seed was harvested from transformed plants and stored at 4° C. in Eppendorf tubes with desiccant. Transformants were selected at the $T_1$ stage by sprinkling $T_1$ seed on a flat, cold treating the flats for 2 to 3 days and spraying plants as soon as they germinated with Finale (Basta, glufosinate ammonium), diluted at 1:1000 of an 11.33% solution, followed by subsequent sprayings a day or two apart.

Following sprayings, non-transgenic seedlings produced chlorotic primary leaves and their hypocotyls dehydrated and collapsed, killing the plant. The survivors were counted and segregation data calculated after the non-transgenic plants had died (within two-three weeks following the sprayings). Survivors were transplanted into individual pots for further monitoring.

Images of each pool of plants were recorded using a Digital camera (DC-260), and morphology observations were taken from plants that exhibited an interesting phenotype. These plants were grown until seed was produced, which was collected and sown to yield $T_2$ plants.

The ACTTAG™ line, W000003696 ("PGD") was originally identified as having an inflorescence structure different from wild type Arabidopsis plants. The phenotype in the $T_1$ plants was further described as dark green leaves, variations in leaf lamina and apical dominance.

Interesting $T_1$ plants were grown until they produced $T_2$ seed, which was collected and planted. $T_2$ plants and $T_3$ plants were observed as having the PGD phenotype, characterized by compact stature with curled leaves and downward-oriented ("brevi-pedicel" or "basi-petal") flowers/siliques.

EXAMPLE 2

Characterization of Plants Which Exhibit the PGD Phenotype

A. Genomic DNA Extraction and Analysis

Nucleon™ PhytoPure™ systems from Amersham™ were used to extract genomic DNA from $T_2$ plant tissue.

1.0 g of fresh plant tissue was ground in liquid nitrogen to yield a free flowing powder, then transferred to a 15-ml polypropylene centrifuge tube. 4.6 ml of Reagent 1 from the Nucleon Phytopure kit was added with thorough mixing followed by addition of 1.5 ml of Reagent 2 from the Nucleon Phytopure kit, with inversion until a homogeneous mixture was obtained. The mixture was incubated at 65° C. in a shaking water bath for 10 minutes, and placed on ice for 20 minutes. The samples were removed from the ice, 2 ml of −20° C. chloroform added, mixed and centrifuged at 1300 g for 10 minutes. The supernatant was transferred to a fresh tube, 2 ml cold chloroform, 200 μl of Nucleon PhytoPure DNA extraction resin suspension added and the mixture shaken on a tilt shaker for 10 minutes at room temperature, then centrifuged at 1300 g for 10 minutes. Without disturbing the Nucleon resin suspension layer, the upper DNA containing phase was transferred to a fresh tube, centrifuged at 9500 rpm for 30 minutes to clarify the transferred aqueous phase, an equal volume of cold isopropanol added, the tube gently inverted until the DNA precipitated and then it was pelleted by centrifugation, washed with cold 70% ethanol, pelleted again and air-dried.

DNA extracted from plants with the PGD phenotype (PGD) and from wild type plants (COL-0) was PCR amplified using primers that amplify a 35S enhancer sequence, and primers that amplify a region of the pBluescript vector sequence in pSKI015. Amplification using primers that span the 35S enhancer region resulted in a ladder of products, indicating that all four copies of the 35S enhancer were present. Amplification using primers to the pBluescript vector was done primarily to detect the T-DNA insert(s) in transformed plants and has been optimized for the following conditions: annealing temp: 57° C., 30 cycles [94° C., 30 sec; 57° C., 1 min; 72° C., 1 min] 1 cycle [72° C., 7 min].

The ACTTAG™ line, W000003696 (PGD) was confirmed as positive for the presence of 35S enhancer and pSKI015 vector sequences by PCR, and as positive for Southern hybridization verifying genomic integration of the ACTTAG DNA and showing the presence of a single T-DNA insertion in the transgenic line.

B. Plasmid Rescue

Genomic DNA from $T_2$ plants of insertion line, W000003696 ("PGD"), was digested by restriction enzymes. The restriction fragments were self-ligated and used to transform the *E. coli* cells. The plasmids that contained a full-length pBluescript vector, 4×35S enhancer, and a right border T-DNA flanking genomic DNA fragment were rescued.

More specifically, genomic DNA was digested with Pst I, EcoR I, BamH I, Spe I, Hind III and/or Xho I under standard reaction conditions at 37° C. overnight. Briefly, each restriction enzyme was heat inactivated at 65° C. for 20 minutes, phenol/chloroform and chloroform isoamyl (24:1) extracted once with each, and the ligation reactions were set up containing the reagents set forth below and left at 16° C. overnight.

| | |
|---|---|
| Digested Genomic DNA | 40 μl |
| 5X Ligation Buffer | 50 μl |
| Ligase (Gibcol, 1U/μl) | 10 μl |
| ddH$_2$O | 150 μl |

The ligated DNA was precipitated, resuspended in ddH2O and used to transform *E. coli* SURE cells (Stratagene) via electroporation, with 10 pg of pUC18 plasmid as a control.

The transformation mixture was spread on two LB-plates containing 100 μg/ml ampicillin and incubated overnight at 37° C. Single colonies were picked from the plates and used to start a 5 ml LB-ampicillin broth culture from each colony by culturing overnight at 37° C. The plasmid was extracted from the culture and restriction digested to confirm the size of genomic insertion.

C. Sequencing Of Rescued Plasmids and/or RT-PCR Products

Sequencing was accomplished using a ABI Prism Big-Dye™ Terminator Cycle Sequencing Ready Reaction Kit (PE Applied Biosystem), AmpliTaq DNA Polymerase (Perkin-Elmer), an ABI Prism™ 310 Genetic Analyzer (Perkin-Elmer) and sequence analysis software, e.g., Sequencer™ 3.1.1 or MacVector 6.5.3.

An ABI Prism BigDye™ Terminator Cycle Sequencing Ready Reaction Kit was used to sequence a rescued plasmid using an ABI Prism™ 310 Genetic Analyzer following the protocols from the manufacturer.

The left ends of plasmids rescued were sequenced across the right T-DNA border.

The rescued sequence was subjected to a basic BLASTN search using the sequence comparison program available at the www.ncbi.nlm.nih.gov/BLAST website and a search of the Arabidopsis Information Resource (TAIR) database, available at the Arabidopsis.org website, which revealed sequence identity to BAC clone MUD21. This BAC is mapped to chromosome 5.

Using GENSCAN, five predicted genes were found in the in the vicinity of the T-DNA insertion, (i.e., within ~5–10 kb) and were and were subjected to further characterization by RT-PCR. The RT-PCR results show that "gene 4" was specifically overexpressed in tissue from plants having the PGD phenotype.

Specifically, RNA was extracted from tissues derived from plants exhibiting the PGD phenotype and from wild type COL-0 plants, followed by reverse transcription of mRNA and amplification of partial cDNA sequences using PCR with forward and reverse primers specific to T-DNA flanking gene 4 (SEQ ID NO:1) which was identified following plasmid rescue. RT-PCR was done using primers specific to gene4 and a constitutively expressed actin (positive control) and, as a template, RNA extracted from wild type plants (Wild Type) and 2 plants displaying the PGD phenotype. The results show that plants displaying the PGD phenotype over-expressed the mRNA for gene 4, indicating the enhanced expression of gene 4 is correlated with the PGD phenotype. Another gene in the vicinity of the T-DNA insertion was tested by RT-PCR and found not to be over-expressed in plants displaying the PGD phenotype.

The amino acid sequence predicted from the PGD nucleic acid sequence was determined using GENSCAN and is presented in SEQ ID NO:2. A Basic BLASTP 2.0.11 search using the ncbi.nlm.nih.gov/BLAST website with the predicted amino acid sequence for PGD, presented in SEQ ID NO:2, revealed that the PGD gene encodes a protein of unknown function.

The predicted PAGODA protein sequence was further analyzed using the MOTIF finder program, at the motif.genome.adjp website, and the PSORT II program, at the psort.ims.u-tokyo.acjp website. The analysis indicated that the PAGODA protein structure has a coiled-coil region in the N-terminal portion at amino acids 82–111, and a novel Nuclear Localization Signal (NLS) in the C-terminal portion of the protein, at amino acids 285–301.

The BLAST search results suggest that PGD represents a newly discovered phenotype and function associated with a known DNA sequence found in the Arabidopsis BAC clone MUD21. These results suggest that PGD is associated with stature and leaf and floral organ morphology in Arabidopsis.

EXAMPLE 3

Confirmation of PGD Dominant Inheritance Pattern

The dominant inheritance pattern of the PAGODA phenotype was confirmed through genetic analysis. In general, genetic analysis involves the production and analysis of $F_1$ hybrids. Typically, $F_1$ crosses are carried out by collecting pollen from $T_2$ plants which is used to pollinate wild type plants. Such crosses are carried out by taking approximately 4 flowers from each selected individual plants, using the $T_2$ flower as the male pollen donor and flowers of the wild type plants as the female. 4–5 crosses are done for an individual of interest. Seed formed from crosses of the same individual are pooled, planted and grown to maturity as $F_1$ hybrids.

Seeds are also collected from the corresponding $T_2$ plants and planted and grown to maturity as a $T_3$ generation for comparison to the $F_1$ hybrid. If all individuals of an $F_1$ hybrid pool exhibit the desired phenotype it is determined that the parental $T_2$ line was homozygous for the trait and that the trait is dominant.

The generation of $F_1$ hybrids from homozygous PGD parents resulted in all the $F_1$ plants exhibiting the PGD phenotype indicating that the PGD phenotype is dominant.

EXAMPLE 4

Confirmation of Phenotype/Genotype Association in Arabidopsis

In order to further confirm the association between the PGD phenotype and the PGD gene presented in SEQ ID NO:1, a genomic fragment comprising the PGD gene, provided in SEQ ID NO:3, was over-expressed in wild type Arabidopsis plants. The PGD fragment, operably linked to the 4×-35S CaMV enhancer fragment, was cloned from Line W000003696 plants. Specifically, this 3920bp genomic fragment, including the promoter and PGD coding regions, was rescued (cloned) from the T-DNA right border by Xho I digestion of genomic DNA. A BamH I and Kpn I fragment that included the 3920 bp PGD fragment and the 4× enhancer was cloned into Bgl II and Kpn I site in the multiple cloning site (MCS) of the binary vector pAGI4002. pAGI4002, whose sequence is provided in SEQ ID NO:4, comprises the vector backbone from the binary vector pPZP200 (GI506655), T-DNA left and right border fragments, and, between border fragments, the MCS and a CsVMV promoter-driven neomycin phosphotransferase (NPTII) gene, which confers kanamycin resistance. The pAGI4002-PGD construct was transformed into *Agrobacterium tumefaciens* by electroporation.

Wild type Arabidopsis (COL-0) plants were transformed with pAGI4002-PGD using standard vacuum infiltration methods. All infiltrated seeds were plated in selective media (60 μg/ml kanamycin), and kanamycin-resistant $T_1$ plants were transplanted to 72-cell flats. Morphological observations demonstrated that a large number of $T_1$ plants had the same strong phenotype with curled leaf and flowers bent down as the original ACTTAG mutant PAGODA. Tissue was collected from six $T_1$ plants showing different degrees of PGD phenotype—four plants showed a strong PGD phenotype, and two showed a weak phenotype—and RT-PCR was carried out using wild type as control. The four $T_1$ lines with strong phenotype showed a very high level accumulation of PGD transcripts, whereas the weak phenotype individuals have much less and wild type showed no detectable PGD transcripts. The internal control experiments using the actin gene showed all samples having the same level of actin expression.

EXAMPLE 5

Confirmation of Phenotype/Genotype Association in Micro-tomato

In order to further confirm the association between the PGD phenotype and the PGD gene in plants other than Arabidopsis, particularly in fruit-bearing plants, the PGD gene was introduced into and over-expressed in wild type *Lycopersicum esculentum* (Micro-Tom) plants.

The pAGI4002-PGD construct described above was introduced into wild-type Micro-Tom plants via Agrobacterium-mediated transformation, essentially as described in PCT application WO0053794. Briefly, explants were dissected from Micro-Tom seedlings. Explants were inoculated by soaking in the Agrobacterium suspension for 15 to 120 minutes, blotted on sterile filter paper to remove excess bacteria, and plated. Explants were co-cultivated in non-selective media for 2–4 days at 24° C. with a 16-hour photoperiod, after which they were transferred to selective media (with kanamycin) and returned to the growth room. Explants were transferred to fresh medium every two weeks until shoots were 0.5 to 1 cm tall. Shoots were excised from the explants, placed on selective medium with kanamycin in Phytatrays (Sigma), and returned to the growth room for two to four weeks. Shoots were observed for rooting, and rooted shoots were out-planted to soil and acclimated to the greenhouse. The transformation process generated 25 independent To events. Morphological observations demonstrated that one event had the same strong phenotype with curled, pendulous leaf as the original Arabidopsis PAGODA mutant, ACTTAG line W000003696.

EXAMPLE 6

PGD Pathway Analysis

A recessive mutant of similar phenotype, bp-1 (brevipedicellus), which was obtained via EMS mutagenesis, has been reported in the literature and is mapped in chromosome 4 (Koornneef et al., 1983). To determine if PGD is in the same signaling pathway as BP-1, we ordered bp-1 seeds (stock #: cs-30) from Arabidopsis Biological Resources Center (ABRC, Columbus, Ohio). Seeds were planted in the growth room, with conditions of 16 hr/8 hr of Light/Dark and 75° F. RNA was extracted from both wild type and bp-1 flower stems. RT-PCR was performed using 45 cycles of PCR and showed that PGD is detected in bp-1 plants and but not in wild type. Results suggested that PGD and BP-1 may be in the same signaling pathway and that BP-1 may negatively regulate PGD expression.

REFERENCES

Altschul, S. F. et al, *J. Mol. Biol.* 215:403–410, 1990.

Altschul, S. F. et al., *Nucleic Acids Res.* 25:3389–3402, 1997.

Ausubel FM et al. Current Protocols in Molecular Biology, John Wiley & Sons, New York, N.Y., 1993.

Baldwin D et al., *Cur Opin Plant Biol.* 2(2):96–103, 1999.

Baulcombe D, *Arch Virol Suppl* 15:189–201, 1999.

Behringer and Medford, *Plant Mol. Biol. Rep.* 10(2): 190–198, 1992.

Carter et al., *Nucl. Acids Res.* 13:4331, 1986.

Christensen S et al., 9$^{th}$ International Conference on Arabidopsis Research. Univ. of Wisconsin-Madison, Jun. 24–28, 1998. Abstract 165.

Cough, S J and Bent, A F, the *Plant Journal* 16(6): 735–743, 1998.

Crameri A and Stemmer W P, *Bio Techniques* 18(2): 194–6, 1995.

Creighton, T. E., *PROTEINS: STRUCTURE AND MOLECULAR PROPERTIES*, W. H. Freeman & Co., San Francisco, pp. 79–86, 1983.

Doolittle, R. F., OF *URFS* and *ORFS* (University Science Books, CA, 1986.)

Fang G et al., *Plant Cell.*, 1(1):141–50, 1989.

Feldman et al., *Science* 243: 1351–1354, 1989.

Fridborg I et al., *Plant Cell* 11: 1019–1032, 1999.

Geest A H and Hall T C, *Plant Mol Biol* 32(4):579–88, 1996).

Gelvin, S. B., Schilperoort, R. A., Varma, D. P. S., eds. Plant Molecular Biology Manual 1990.

Glick, B R and Thompson, J E, Eds. METHODS IN PLANT MOLECULAR BIOLOGY AND BIOTECHNOLOGY, p. 213–221, CRC Press, 1993.

Harling et al., *EMBO J.* 16: 5855–66, 1997.

Haught C et al. *BioTechniques* 16(1):47–48, 1994.

Hayashi H et al., *Science* 258: 1350–1353, 1992.

Jakobovits, A, et al., Ann NY Acad Sci 764:525–35, 1995.

Jakobovits, A, Curr Opin Biotechnol 6(5):561–6, 1995.

Jensen, L. G., et al., *Proc. Natl. Acad. Sci. USA* 93:3487–3491, 1996.

Jones et al., *Nature* 321:522–525, 1986.

Jones J D et al, Transgenic Res 1:285–297 1992.

Kakimoto, Science 274: 982–5, 1996.

Kardailsky, I et al., *Science* 286: 1962–1965, 1998.

Kardailsky et al., *Science* 286: 1962–5, 1999.

Kohler and Milstein, *Nature* 256:495, 1975.

Kunkel T A et al., *Methods Enzymol.* 204:125–39, 1991.

Liu et al. *Plant Journal* 8(3) 457–463, 1995.

Maniatis, et al., MOLECULAR CLONING: A LABORATORY MANUAL, 2d Edition, 1989.

Marks and Feldman, *Plant Cell* 1: 1053–1050, 1989.

Miklashevichs et al. *Plant J.* 12: 489–98, 1997.

Napoli, et al, *Plant Cell* 2:279–289, 1989.

Novak, J and Novak, L, *Promega Notes Magazine Number* 61:27, 1997.

Omirulleh et al., Plant Mol Biol. 21(3):415–28, 1993.

Riechmann et al., *Nature* 332:323–327, 1988.

Sambrook et al. Molecular Cloning: A Laboratory Manual (Second Edition), Cold Spring Harbor Press, Plainview, N.Y.,1989.

Schaffer R, et al., *Cell* 93: 1219–1229, 1998.

Schell et al., Trends Plant Sci. 3: 130, 1998.

Smith, et al., *Nature* 334:724–726, 1988.

Van Haaren M J J et al., Plant Mol Bio 21:625–640, 1993.

Verdaguer B et al., Plant Mol Biol 37:1055–1067, 1998.

Verhoeyen et al., *Science* 239:1534–1536, 1988.

Walden et. al., EMBO J. 13: 4729–36, 1994.

Walden et al., *Plant Mol. Biol.* 26: 1521–8, 1994.

Waterhouse, et al., *Proc. Natl. Acad. Sci. USA* 95:13959–13964, 1998.

Wells et al., *Gene* 34:315, 1985.

Wells et al., *Philos. Trans. R. Soc. London Ser A* 317:415, 1986.

Weigel D, et al., *Plant Physiology,* 122:1003-1-13, 2000.

Wilson K et al., *Plant Cell* 8: 659–671, 1996.

Xu Y L, et al., *Plant Cell,* 11: 927–36, 1999.

Zoller et al., *Nucl. Acids Res.* 10:6487, 1987.

It is claimed:

1. An isolated polynucleotide comprising a nucleic acid sequence which encodes or is complimentary to a sequence which encodes a PAGODA polypeptide that has the amino acid sequence presented as SEQ ID NO:2.

2. The polynucleotide of claim 1 comprising the nucleic acid sequence presented as SEQ ID NO:1.

3. A plant transformation vector comprising the isolated polynucleotide of claim 1.

4. A transgenic plant cell comprising the vector of claim 3.

* * * * *